United States Patent
Ribeiro, Jr.

(10) Patent No.: US 6,691,043 B2
(45) Date of Patent: Feb. 10, 2004

(54) BOLUS CALCULATOR

(75) Inventor: Jose' Carlos Ribeiro, Jr., Kissimmee, FL (US)

(73) Assignee: Maxi-Med, LLC, Braselton, GA (US)

( * ) Notice: Subject to any disclaimer, the term of this patent is extended or adjusted under 35 U.S.C. 154(b) by 0 days.

(21) Appl. No.: 09/941,011

(22) Filed: Aug. 28, 2001

(65) Prior Publication Data

US 2003/0055570 A1 Mar. 20, 2003

(51) Int. Cl.[7] .................. G01N 33/50; A61B 5/00
(52) U.S. Cl. ............... 702/19; 600/300; 600/316; 600/365; 604/67; 702/23
(58) Field of Search ................ 702/19, 22, 23; 600/300, 316, 365; 604/67

(56) References Cited

U.S. PATENT DOCUMENTS

| | | | |
|---|---|---|---|
| 5,019,974 A | 5/1991 | Beckers | 600/316 |
| 5,822,715 A | 10/1998 | Worthington et al. | 702/19 |
| 5,997,475 A | 12/1999 | Bortz | 600/300 |
| 6,269,314 B1 * | 7/2001 | Iitawaki et al. | 702/23 |
| 6,425,863 B1 * | 7/2002 | Werner et al. | 600/365 |

OTHER PUBLICATIONS

Mann et al., "External infusion device with remote programming, bolus estimator and/or vibration alrm capabilities", Pub. No.: US2002/0107476, Pub. Date: Aug. 8, 2002.*

Robinton, "How to measure Blood Sugar to Insulin ratio", v1.04, Feb. 6, 1998. Retrieved from Internet electronic mail:<Michael@bzs.org>.*

Pecoraro, "Carbohydrate Counting and Insulin Ajustment", Novo Nordisk Pharmaceuticals, Inc., Jul. 2001.*

Nowizky, "Insulin Bolus Calculation Form", Aug. 10, 1997, NowizKonsult Co.*

* cited by examiner

Primary Examiner—John Barlow
Assistant Examiner—John Le (57) ABSTRACT

The invention calculates the precise amount of insulin needed by someone (the user) who is diabetic and/or insulin/insulin-pump user, in order to keep the user's blood sugar concentration in the previously set target, and provides a practical method to make the necessary changes (weekly, monthly, every other month, etc) in the personal carbohydrate ratio profile, and more specifically the invention, calculates the user's carbohydrate ratio at any given time and allows the user to determine the amount of insulin (Bolus) to be injected.

8 Claims, 8 Drawing Sheets

FIG.1

RP: Ratio Points

RF: Ratio Function

BC: Bolus Calculator

TI: Typed-in field     C: Calculated field

| A | B | C | D | E | F | G | H | J | L |
|---|---|---|---|---|---|---|---|---|---|
| TI | C | TI | TI | TI | TI | C | C | TI | C |
| 8:00AM | 8.00 | 56 | 110 | 12.00 | 12 | 4.9 | 4.9 | 281 | 6.03 |
| 10:00AM | 10.00 | 60 | 95 | 12.00 | 12 | 4.9 | 4.9 | 200 | 7.94 |
| 12:00AM | 12.00 | 45 | 120 | 12.00 | 12 | 4.3 | 4.3 | 145 | 9.18 |
| 1:30PM | 13.50 | 46 | 112 | 12.00 | 12 | 4.1 | 4.1 | 101 | 11.92 |
| 3:30PM | 15.50 | 23 | 70 | 12.00 | 12 | 1.2 | 1.2 | 89 | 14.06 |
| 5:30PM | 17.50 | 63 | 115 | 12.00 | 12 | 5.6 | 5.6 | 59 | 14.99 |

| V1 | V2 | V3 | V4 | V5 | V6 | V7 |
|---|---|---|---|---|---|---|
| TI | TI | TI | C | C | TI | C |
| 100.00 | 46.00 | 21.00 | 45.98 | 39.13 | 46.00 | 39.13 |

B <----- decimal time (from A)      G <----- ((C/E)+(D-V1)/V7)
V5 <----- 1800/V2      H <----- ((C/E)+(D-V1)/V5)
V7 <----- 1800/V6      V4 <----- SUM(H)
     L <----- C/(((D-V1)/V5)+(D/E))

SEQUENCE TO COMPLETE THE FIELDS (TYPING IN AND CALCULATING):

1) Typing Sequence: V1, V2, V3, V6, A, C, D, E, F, J

2) Calculation Sequence: B, V5, V7, G, H, V4, L

| A | B | C | D | E | F |
|---|---|---|---|---|---|
| Time | Time (decimal) | Carbohydrates | Before-meal Blood Sugar | Variable Carbohydrate Ratio | Fixed Carbohydrate Ratio |
| 5:00AM | 5.00 | 56 | 110 | 12.00 | 12 |
| 12:00AM | 12.00 | 60 | 95 | 12.00 | 12 |
| 3:00PM | 15.00 | 45 | 120 | 12.00 | 12 |
| 6:15PM | 18.25 | 46 | 112 | 12.00 | 12 |
| 8:30PM | 20.50 | 23 | 70 | 12.00 | 12 |
| 10:30PM | 22.50 | 63 | 115 | 12.00 | 12 |

| G | H | I | J | K | L |
|---|---|---|---|---|---|
| Traditional Bolus | Proposed Bolus | Insulin Delta | Prandial Blood Sugar (Proposed) | Prandial Blood Sugar (Traditional) | Calculated Carbohydrate Ratio |
| 4.9 | 4.9 | 0.0 | 281 | 281 | 6.03 |
| 4.9 | 4.9 | 0.0 | 200 | 200 | 7.94 |
| 4.3 | 4.3 | 0.0 | 145 | 145 | 9.18 |
| 4.1 | 4.1 | 0.0 | 101 | 101 | 11.92 |
| 1.2 | 1.2 | 0.0 | 89 | 89 | 14.06 |
| 5.6 | 5.6 | 0.0 | 59 | 59 | 14.99 |

| | | |
|---|---|---|
| Target Blood Sugar Level (mg/dL) | 100.00 | V1 |
| Adopted Total Amount of Insulin (Bolus+Basal Rate) | 46.00 | V2 |
| Total Amount of Insulin through Basal Rate | 21.00 | V3 |
| Units of insulin per day (Proposed Way) | 45.98 | V4 |
| Variable Insulin Sensitivity (VIS) - (Proposed Way) | 39.13 | V5 |
| Insulin per day - fixed (Traditional Way) | 46.00 | V6 |
| Fixed Insulin Sensitivity (FIS) - (Traditional Way) | 39.13 | V7 |
| Traditional Bolus | EQUATION 14 | V8 |
| Proposed Bolus | EQUATION 13 | V9 |
| Insulin Delta between Traditional and Proposed Boluses | 0.00 | V10 |
| Expected Prandial Blood Sugar (Traditional Way) | EQUATION 2 | V11 |
| Calculated Carbohydrate Ratio | EQUATION 3 | V12 |
| Standard Deviation from Target - mg/dL (Proposed Way) | 77.23 | V13 |
| Standard Deviation from Target - mg/dL (Traditional Way) | 77.23 | V14 |

FIG.4

| A | B | C | D | E | F |
|---|---|---|---|---|---|
| Time | Time (decimal) | Carbohydrates | Before-meal Blood Sugar | Variable Carbohydrate Ratio | Fixed Carbohydrate Ratio |
| 5:00AM | 5.00 | 53 | 131 | 6.03 | 12 |
| 12:00AM | 12.00 | 88 | 88 | 7.94 | 12 |
| 3:00PM | 15.00 | 24 | 84 | 9.18 | 12 |
| 6:15PM | 18.25 | 16 | 81 | 11.92 | 12 |
| 8:30PM | 20.50 | 110 | 70 | 14.06 | 12 |
| 10:30PM | 22.50 | 60 | 62 | 14.99 | 12 |

| G | H | I | J | K | L |
|---|---|---|---|---|---|
| Traditional Bolus | Proposed Bolus | Insulin Delta | Prandial Blood Sugar (Proposed) | Prandial Blood Sugar (Traditional) | Calculated Carbohydrate Ratio |
| 5.2 | 9.7 | -4.5 | 102 | 253 | 5.99 |
| 7.0 | 10.7 | -3.7 | 98 | 221 | 7.98 |
| 1.6 | 2.1 | -0.5 | 101 | 119 | 9.08 |
| 0.8 | 0.8 | 0.1 | 100 | 97 | 11.92 |
| 8.4 | 6.9 | 1.5 | 101 | 52 | 14.01 |
| 4.0 | 2.9 | 1.2 | 100 | 61 | 14.99 |

| | | |
|---|---|---|
| Target Blood Sugar Level (mg/dL) | 100.00 | V1 |
| Adopted Total Amount of Insulin (Bolus+Basal Rate) | 54.00 | V2 |
| Total Amount of Insulin through Basal Rate | 21.00 | V3 |
| Units of insulin per day (Proposed Way) | 54.14 | V4 |
| Variable Insulin Sensitivity (VIS) - (Proposed Way) | 33.33 | V5 |
| Insulin per day - fixed (Traditional Way) | 46.00 | V6 |
| Fixed Insulin Sensitivity (FIS) - (Traditional Way) | 39.13 | V7 |

| | | |
|---|---|---|
| Traditional Bolus | EQUATION 14 | V8 |
| Proposed Bolus | EQUATION 13 | V9 |
| Insulin Delta between Traditional and Proposed Boluses | -6.03 | V10 |
| Expected Prandial Blood Sugar (Traditional Way) | | V11 |
| Calculated Carbohydrate Ratio | EQUATION 2 | V12 |
| Standard Deviation from Target - mg/dL (Proposed Way) | EQUATION 3 | V13 |
| Standard Deviation from Target - mg/dL (Traditional Way) | 1.25 | V13 |
| | 77.74 | V14 |

FIG.5

| A | B | C | D | E | F |
|---|---|---|---|---|---|
| Time | Time (decimal) | Carbohydrates | Before-meal Blood Sugar | Variable Carbohydrate Ratio | Fixed Carbohydrate Ratio |
| 5:00AM | 5.00 | 48 | 87 | 5.99 | 12 |
| 12:00AM | 12.00 | 42 | 81 | 7.98 | 12 |
| 3:00PM | 15.00 | 46 | 84 | 9.08 | 12 |
| 6:15PM | 18.25 | 44 | 106 | 11.92 | 12 |
| 8:30PM | 20.50 | 120 | 71 | 14.01 | 12 |
| 10:30PM | 22.50 | 48 | 72 | 14.99 | 12 |

| G | H | I | J | K | L |
|---|---|---|---|---|---|
| Traditional Bolus | Proposed Bolus | Insulin Delta | Prandial Blood Sugar (Proposed) | Prandial Blood Sugar (Traditional) | Calculated Carbohydrate Ratio |
| 3.7 | 7.6 | -4.0 | 99 | 237 | 6.01 |
| 3.0 | 4.7 | -1.7 | 100 | 159 | 7.98 |
| 3.4 | 4.6 | -1.2 | 101 | 142 | 9.03 |
| 3.8 | 3.9 | 0.0 | 99 | 101 | 12.01 |
| 9.3 | 7.7 | 1.5 | 99 | 46 | 14.06 |
| 3.3 | 2.4 | 0.9 | 100 | 69 | 14.99 |

| | | |
|---|---|---|
| Target Blood Sugar Level (mg/dL) | 100.00 | V1 |
| Adopted Total Amount of Insulin (Bolus+Basal Rate) | 52.00 | V2 |
| Total Amount of Insulin through Basal Rate | 21.00 | V3 |
| Units of insulin per day (Proposed Way) | 51.94 | V4 |
| Variable Insulin Sensitivity (VIS) - (Proposed Way) | 34.62 | V5 |
| Insulin per day - fixed (Traditional Way) | 46.00 | V6 |
| Fixed Insulin Sensitivity (FIS) - (Traditional Way) | 39.13 | V7 |
| Traditional Bolus | EQUATION 14 | V8 |
| Proposed Bolus | EQUATION 13 | V9 |
| Insulin Delta between Traditional and Proposed Boluses | -4.47 | V10 |
| Expected Prandial Blood Sugar (Traditional Way) | EQUATION 2 | V11 |
| Calculated Carbohydrate Ratio | EQUATION 3 | V12 |
| Standard Deviation from Target - mg/dL (Proposed Way) | 0.76 | V13 |
| Standard Deviation from Target - mg/dL (Traditional Way) | 63.76 | V14 |

FIG.6

| A | B | C | D | E | F |
|---|---|---|---|---|---|
| Time | Time (decimal) | Carbohydrates | Before-meal Blood Sugar | Variable Carbohydrate Ratio | Fixed Carbohydrate Ratio |
| 5:00AM | 5.00 | 45 | 150 | 6.01 | 12 |
| 12:00AM | 12.00 | 23 | 76 | 7.98 | 12 |
| 3:00PM | 15.00 | 45 | 84 | 9.03 | 12 |
| 6:15PM | 18.25 | 40 | 109 | 12.01 | 12 |
| 8:30PM | 20.50 | 43 | 75 | 14.06 | 12 |
| 10:30PM | 22.50 | 100 | 126 | 14.99 | 12 |

| G | H | I | J | K | L |
|---|---|---|---|---|---|
| Traditional Bolus | Proposed Bolus | Insulin Delta | Prandial Blood Sugar (Proposed) | Prandial Blood Sugar (Traditional) | Calculated Carbohydrate Ratio |
| 5.0 | 8.9 | -3.9 | 100 | 239 | 6.01 |
| 1.3 | 2.2 | -0.9 | 99 | 132 | 8.06 |
| 3.3 | 4.5 | -1.2 | 99 | 142 | 9.08 |
| 3.6 | 3.6 | 0.0 | 100 | 101 | 12.01 |
| 2.9 | 2.4 | 0.6 | 101 | 80 | 13.93 |
| 9.0 | 7.4 | 1.6 | 100 | 42 | 14.99 |

| | | | |
|---|---|---|---|
| Target Blood Sugar Level (mg/dL) | 100.00 | V1 | |
| Adopted Total Amount of Insulin (Bolus +Basal Rate) | 50.00 | V2 | |
| Total Amount of Insulin through Basal Rate | 21.00 | V3 | |
| Units of insulin per day (Proposed Way) | 49.97 | V4 | |
| Variable Insulin Sensitivity (VIS) - (Proposed Way) | 36.00 | V5 | |
| Insulin per day - fixed (Traditional Way) | 46.00 | V6 | |
| Fixed Insulin Sensitivity (FIS) - (Traditional Way) | 39.13 | V7 | |
| Traditional Bolus | | V8 | EQUATION 14 |
| Proposed Bolus | | V9 | EQUATION 13 |
| Insulin Delta between Traditional and Proposed Boluses | -3.79 | V10 | |
| Expected Prandial Blood Sugar (Traditional Way) | | V11 | EQUATION 2 |
| Calculated Carbohydrate Ratio | | V12 | EQUATION 3 |
| Standard Deviation from Target - mg/dL (Proposed Way) | 0.69 | V13 | |
| Standard Deviation from Target - mg/dL (Traditional Way) | 62.09 | V14 | |

BOLUS CALCULATOR

BACKGROUND OF THE INVENTION

For human beings, normal amounts of glucose concentration in the bloodstream are considered between 70 and 126 mg/dl—higher concentration of glucose are prone to cause clogged arteries, urinary infections, retina and kidney damage, etc. Diabetes is a chronic disease related with high amounts of glucose in the bloodstream. American Diabetes Association research shows that there are 135 million diabetic people in the world, and 10% have type-I diabetes (13.5 million people). In the USA nearly 16 million people have diabetes, as follows:

2 million people have type-1 diabetes (1 million diagnosed and 1 million undiagnosed).

14 million people have type-2 diabetes (7 million diagnosed and 7 million undiagnosed), Every day 2,000 cases of diabetes are diagnosed. Per year, $92 billion dollars are spent by the US government on diabetes—$47 billion dollars only for diabetes-related health problems, such as heart and kidney diseases, amputations, blindness, etc. Diabetes is the US sixth leading cause of death. Tight control of blood sugar level reduces complications by 75%. Currently the most advanced treatment for diabetes is the Insulin Pump, however, most users do not have a practical way to determine the correct amount of insulin that should be injected by the pump.

The insulin pump mimics the human pancreas by constantly injecting, in a paced way, small amounts of insulin throughout the day through a plastic tube inserted in the user's abdomen. This paced activity is called basal rate and its intention is to supply the necessary amount of insulin to the human body cells in order to burn glucose, which keeps the whole organism working. When food is ingested, a larger amount of insulin (bolus) is required for the glucose digestion inside the cells—insulin allows glucose to go inside the cells to be digested. This activity is how energy is produced in the body. The main point of this invention is to disclose an innovative way to determine the right amount of insulin for a bolus. This invention requires an insulin user to determine his/her basal rate. The basal rate is not determined by this invention. The user is required to add the total amount of insulin used for his/her basal rate with the total used for his/her bolus, throughout the day, to use the invention. In 2001, the Insulin Pump market is 125,000 units in the US; 100,000 units in Europe; and 250,000 units worldwide. Type-2 diabetes could also be treated with a pump in the near future, which could make the potential market for this invention increase seven (7) times. This invention provides a way to calculate the correct amount of insulin needed by someone who is a diabetic and/or insulin/insulin-pump user.

BRIEF SUMMARY OF THE INVENTION

Function of this invention performed by the prior work: not applicable. The users did not have a practical way to determine their bolus with exactness, as well as they did not have a practical way to set up carbohydrate ratio profiles on a monthly, weekly or even a daily basis.

Disadvantages of the prior work:

Unstable blood sugar. A small amount of insulin, such as 1/10 of an unit, is very important, and manual calculations do not provide the required exactness such as decimal precision in a day-by-day calculation. A person's carbohydrate absorption changes throughout the day, and the daily pattern can change weekly, or monthly, but for simplicity physicians assume it constant throughout the day and long periods.

Complexity. People who are unable to focus and/or perform complex calculations (such as older and younger people) guess, instead of determine the correct amount of insulin (bolus).

Figure 9:
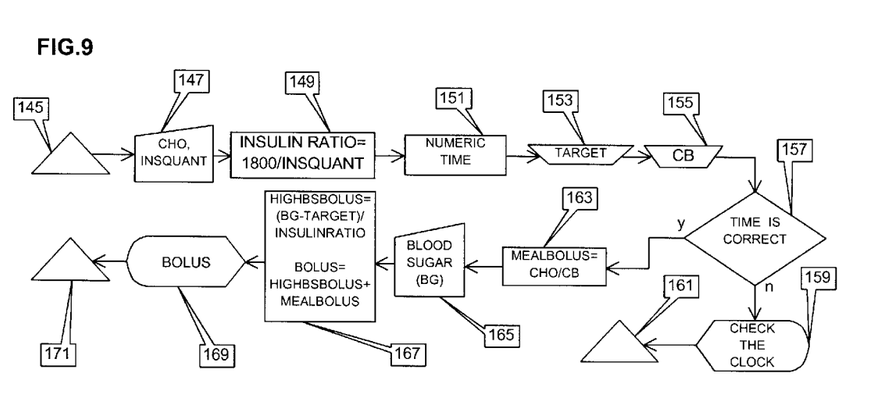
FIG. 9 is a diagram that illustrates how the insulin quantity (bolus) is calculated, in accordance with the invention.

Advantages of this invention over the prior work:

Easy to use. The user is required to enter three data (the blood sugar test reading, the amount of carbohydrates eaten and the amount of insulin he/she forecasts for that day) in order to know the precise amount of insulin required for that meal. If the user's pump can distribute 1/100 of an unit of insulin, the invention can be set up for that precision, as shown by FIG. 9, box 169—whenever a value is shown at the screen or whatever method, the precision of the output can be set at box 169. For example, if the invention is programmed in BASIC, the user must change the number of units of the character # used with instruction PRINTUSING, in order to set up how the result (bolus) will be displayed. The number of units of the character # determines how many units will be shown: one character # before the period mean up to 9 units of insulin displayed; two characters # mean up to 99 units of insulin displayed; one character # after the period mean up to 9 tenths of unit of insulin displayed (0.9 units); two characters # after the period mean up to 0.9 tenths of units of insulin displayed (0.09) units.

Practical Results. People who are unable to focus and/or perform complex calculations (such as older and younger people), will not need to go through manual calculations to determine the correct amount of insulin required for a meal. The invention calculates the precise amount of insulin needed by someone who is diabetic and/or insulin/insulin-pump user and provides a practical method to make the necessary changes (weekly, monthly, every other month, etc) in the personal carbohydrate ratio profile.

DESCRIPTION OF THE INVENTION

The focus of this invention is to obtain the quantity of insulin required by an insulin user, including how many carbohydrates are being eaten at that moment, the blood sugar level at that moment and the amount of insulin he/she forecasts for that day. Designed for short-acting insulin only, an insulin user should understand how he/she individually reacts to insulin over time. This invention requires an insulin user to enter his/her blood sugar level at the correct time intervals related to his/her insulin reaction (1½ hour to 4 hours). Known as prandial blood sugar level, this is the glucose concentration amount after the ingested food was digested. Insulin action varies by user and by insulin—for the one used with pumps, called fast-action insulin, the action is normally from 1½ hour to 4 hours. In order for an user to determine how many units of insulin (bolus) he/she needs to keep his/her blood sugar level within an acceptable value (target) after food ingestion, two parts must be combined:

Result of total amount of carbohydrates eaten divided by the carbohydrate ratio, and The gap between current blood sugar and target blood sugar, divided by the insulin sensitivity.

$$BOLUS=(C/CR)+(BSR-BST)/IS \quad \text{EQUATION 1}$$

C: Total quantity of carbohydrates eaten in the meal BST: Target Blood Sugar

CR: Carbohydrate Ratio IS: Insulin Sensitivity BSR: Blood Sugar Reading

If the blood sugar level is lower than the target, the amount after the plus sign shown in EQUATION 1, will be negative, this will cause a correction in the total amount of insulin, when added with the amount before the plus sign in EQUATION 1.

Figure 2:
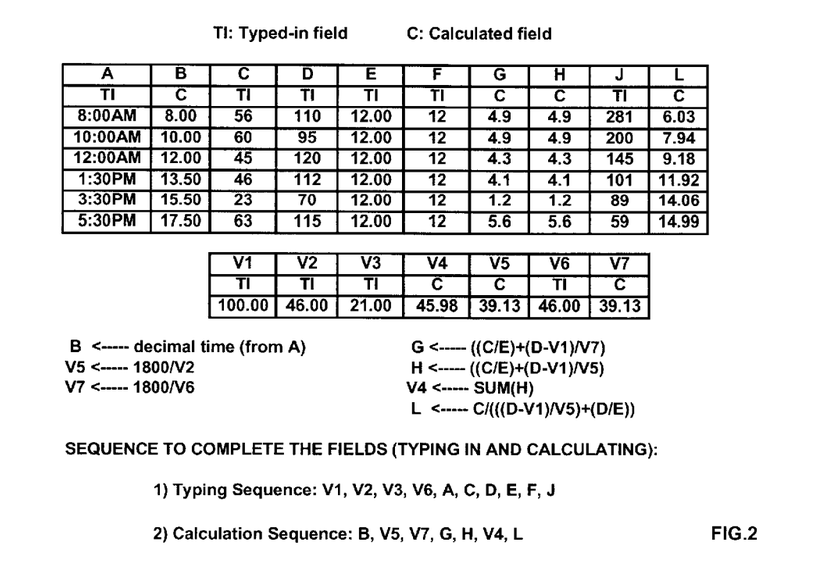
FIG. 2 is a table that facilitates the calculation of the carbohydrate ratio points (item a), in accordance with the invention.

This invention provides a practical way to determine the carbohydrate ratio, as well as make it easily accessible and known throughout the day, since it varies with time. Each user has his/her own carbohydrate ratio profile, so each one must personalize his/her own data. In order to build a Carbohydrate Ratio Function that varies with time, this invention requires points (at least three) that will be interpolated through a $4^{th}$-degree polynomial equation determined by the least squares method and resulting in a function. The user inputs the data needed by sequence shown by FIG. 2, resulting in a customized set of points composed by carbohydrate ratio (column L) versus time (column B). The sequence of FIG. 2 is enough to determine the set of points if he/she follows a regular and steady eating practice during the time he/she is using the invention. However, if the user is constantly changing his/her eating habits, he/she should complete an interactive process (FIG. 3 through FIG. 6) for four days, as seen through item a. User can customize the process going through two, three, five, etc, days, but the preferred embodiment of this invention is for four days.

The user completes an interactive process (FIG. 3 through FIG. 6) for four days (shown through item a), resulting in a customized set of precise data points. Entering the time into the built curve, the result will be a carbohydrate ratio amount for the time entered. Thus, the system executes calculus of EQUATION 13, and determines the amount of insulin. The preferred embodiment of this invention is described as follows, although the Ratio Function (RF) can be determined using similar methods for forecasting (instead of $4^{th}$-degree polynomial equation by the least squares method, use of linear, $2^{nd}$, $3^{rd}$, $5^{th}$, etc degrees for the same method, linear or non-linear regression, Lagrange's Polynomial Equation, and the various other methods available).

Figure 1:
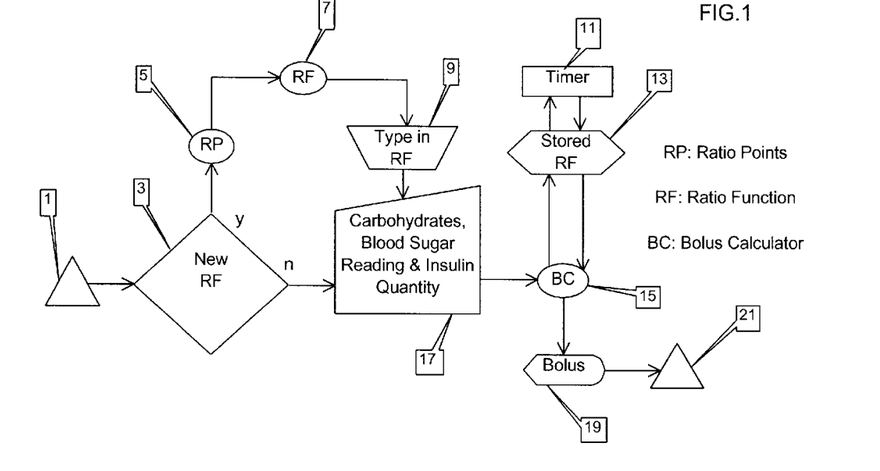
FIG. 1 is a diagram of the integrated system, illustrating how the parts work together, in accordance with the invention.
Figure 7:
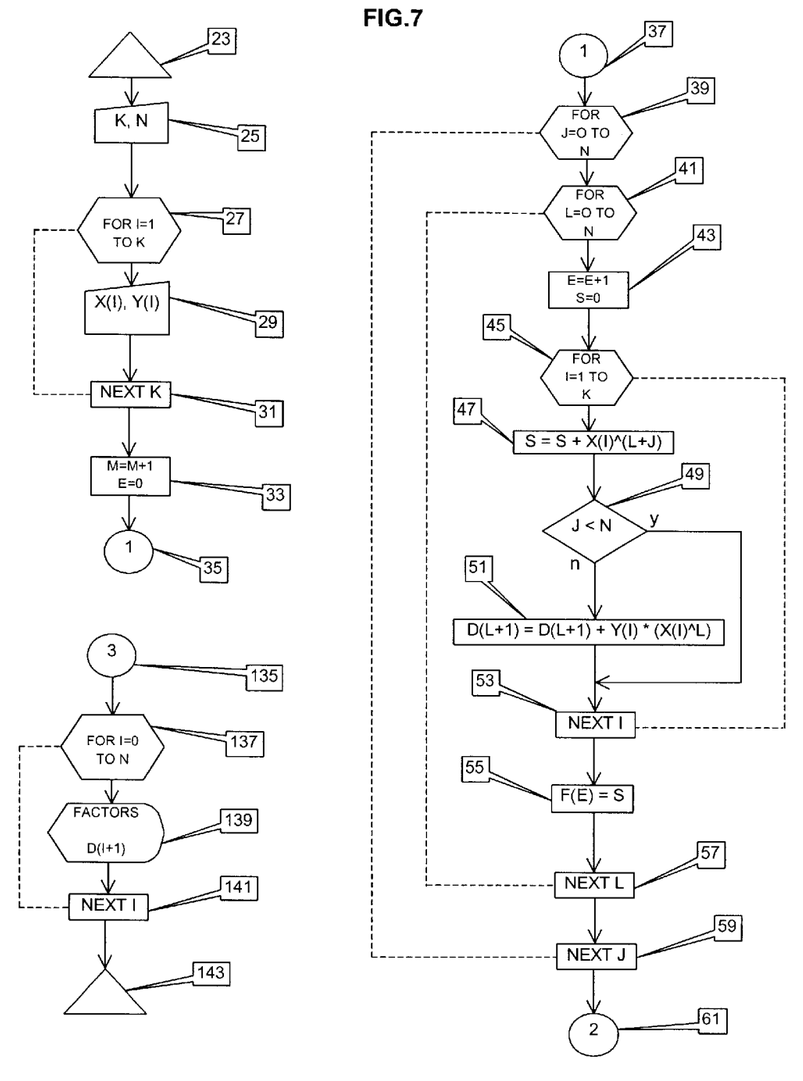
FIG. 7 is a diagram of the interpolation process (item b), illustrating how the carbohydrate ratio points are interpolated in order to determine the carbohydrate ratio curve (item c), in accordance with the invention.
Figure 8:
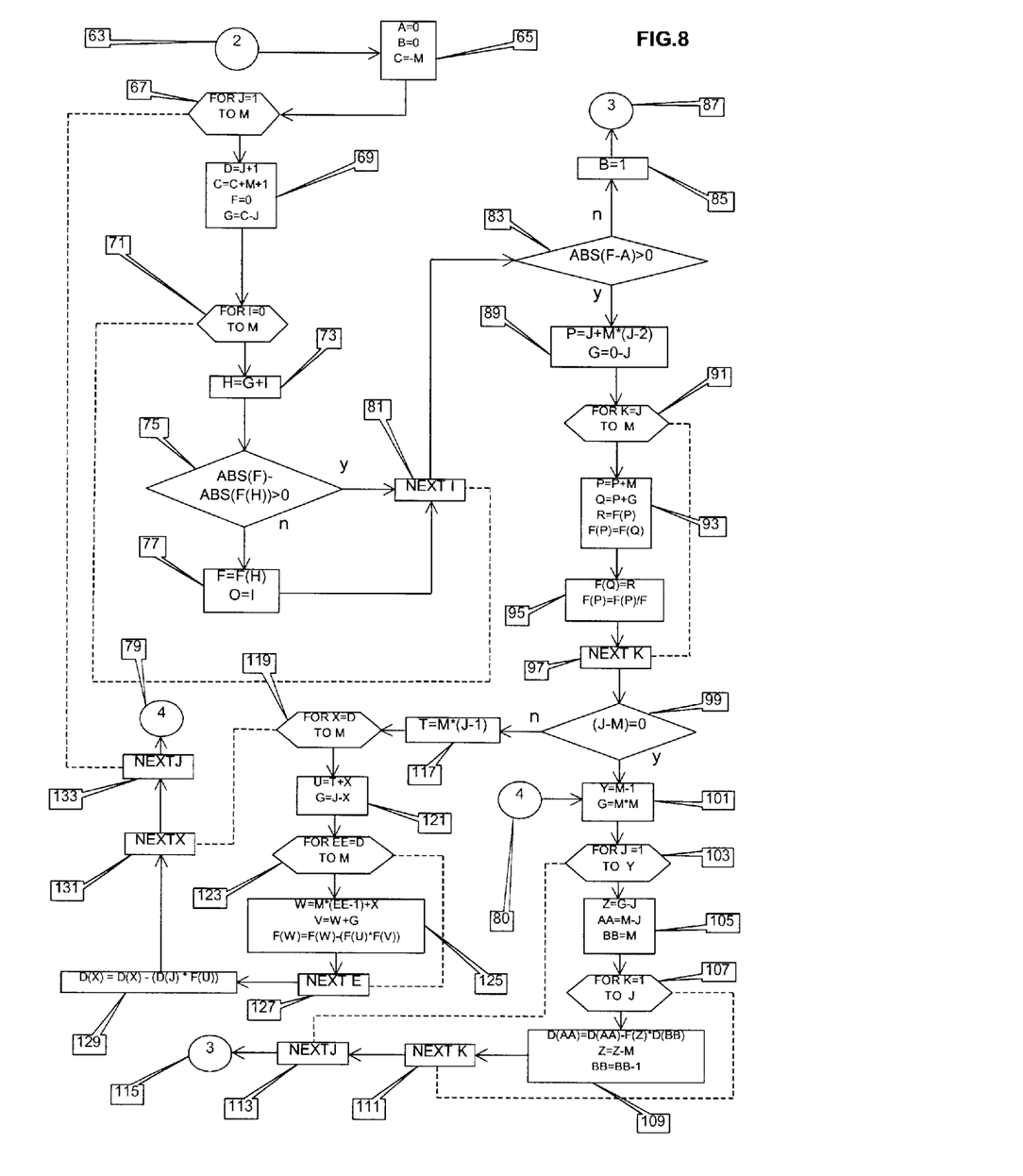
FIG. 8 is a diagram of resolution of a system of equations by the Gauss method, linked from FIG. 7, in accordance with the invention.

The same is valid for the system of equations' resolution (instead of Gauss, use of Gauss-Jordan, Castilho, Substitution and the various other methods available) and for the how the blood sugar reading is determined (normally by home blood sugar monitoring systems, from different brands and models). System has three main parts: a) FIG. 1 shows them integrated as a system; FIG. 2 shows how the carbohydrate ratio points are determined (if user has a regular diet—otherwise the user will go through FIG. 3 through FIG. 6, the complete and interactive procedure); b) FIG. 7 and FIG. 8 show how the carbohydrate curve is built through interpolation, using data from item a; and c) FIG. 9 shows how the quantity of insulin (bolus) is calculated.

To start using this invention the user determines his/her carbohydrate ratio-versus-time set of points, inputs them into an interpolation process, determines a carbohydrate ratio curve and then the user is able to calculate his/her carbohydrate ratio at any given time, and go through a conventional bolus calculation formula—such as EQUATION 13—in order to calculate the bolus. The user goes through either the 1-day method (FIG. 2) or the 4-day method (FIG. 3 through FIG. 6)—depending on his/her eating habits—to determine the set of points (item a) and input it into a function builder (item b; FIG. 7 is interpolation software, and FIG. 8 is a sub-routine for system of equation resolution), resulting in a vector that describes a $4^{th}$-degree polynomial equation that will forecast the user's carbohydrate ratio at any given time. This value, then is used to feed a conventional bolus calculation (item c) that will calculate the bolus, as shown by EQUATION 13.

Figure 3:
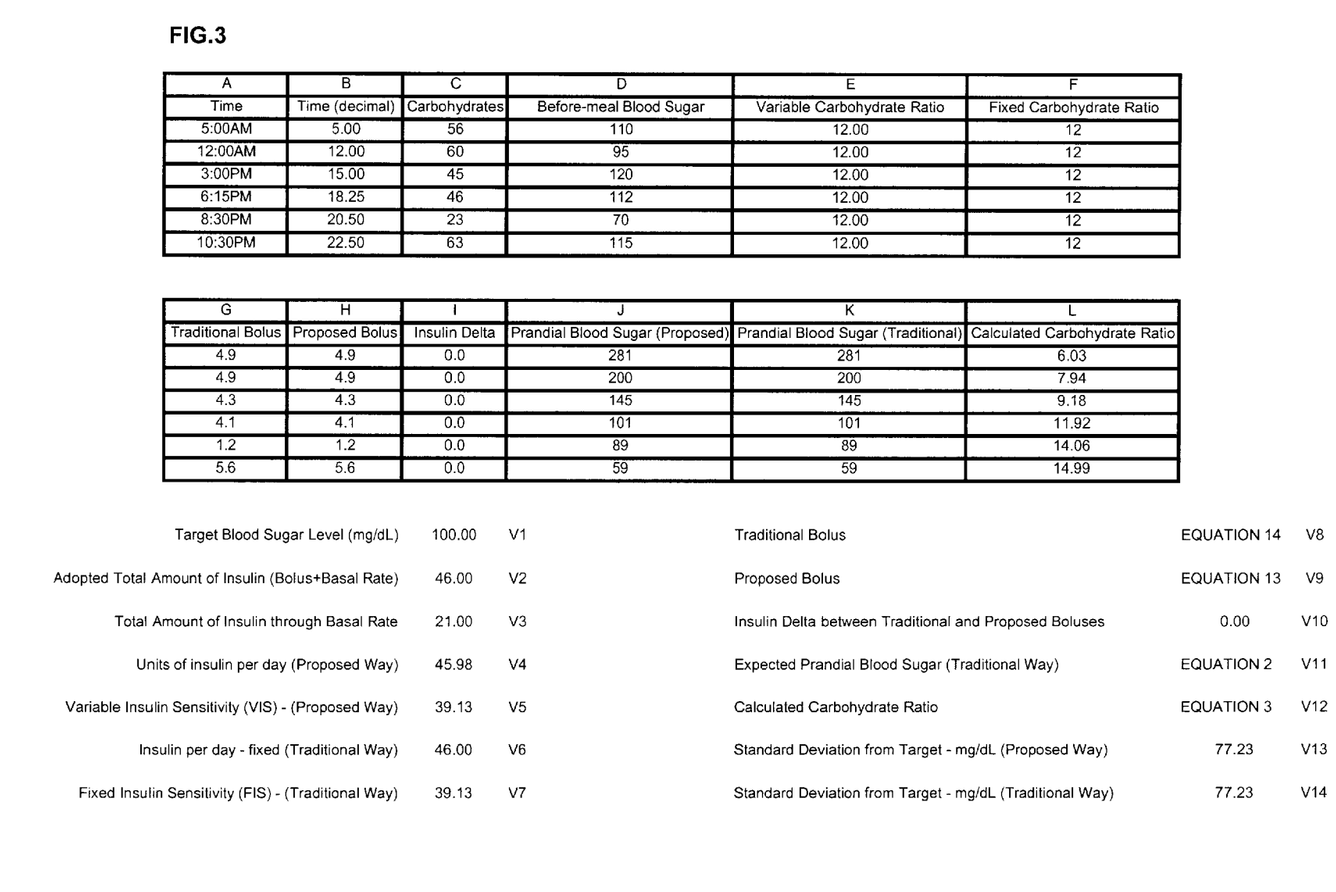
FIG. 3 is a table that facilitates the first interaction of the interactive process that determines the carbohydrate ratio points (item a), whether the user does not have a steady eating habit and he/she needs to go through the 4-day process, in accordance with the invention.
Figure 4:
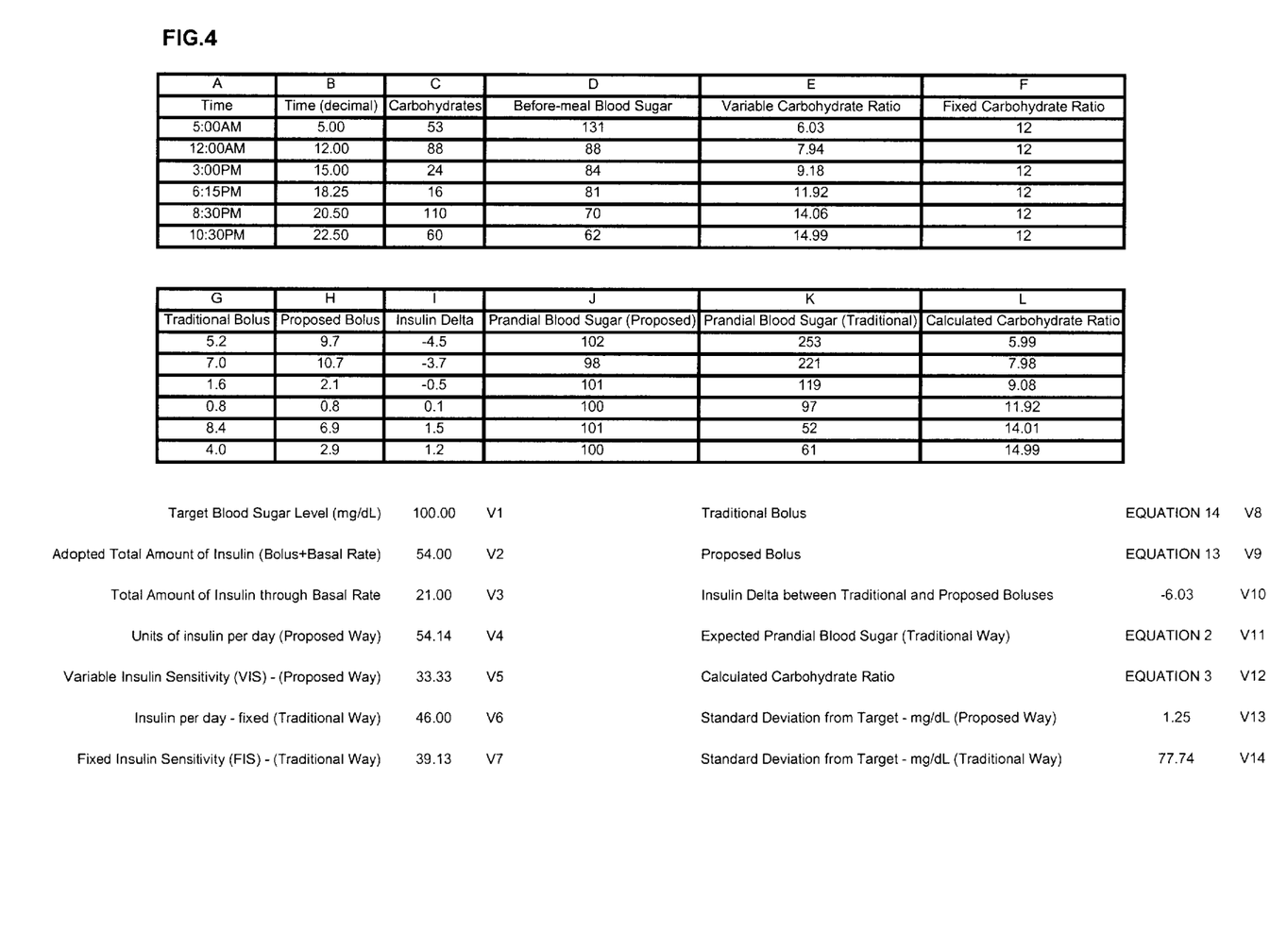
FIG. 4 is a table that facilitates the second interaction of the interactive process that determines the carbohydrate ratio points (item a), whether the user does not have a steady eating habit and he/she needs to go through the 4-day process, in accordance with the invention.
Figure 5:
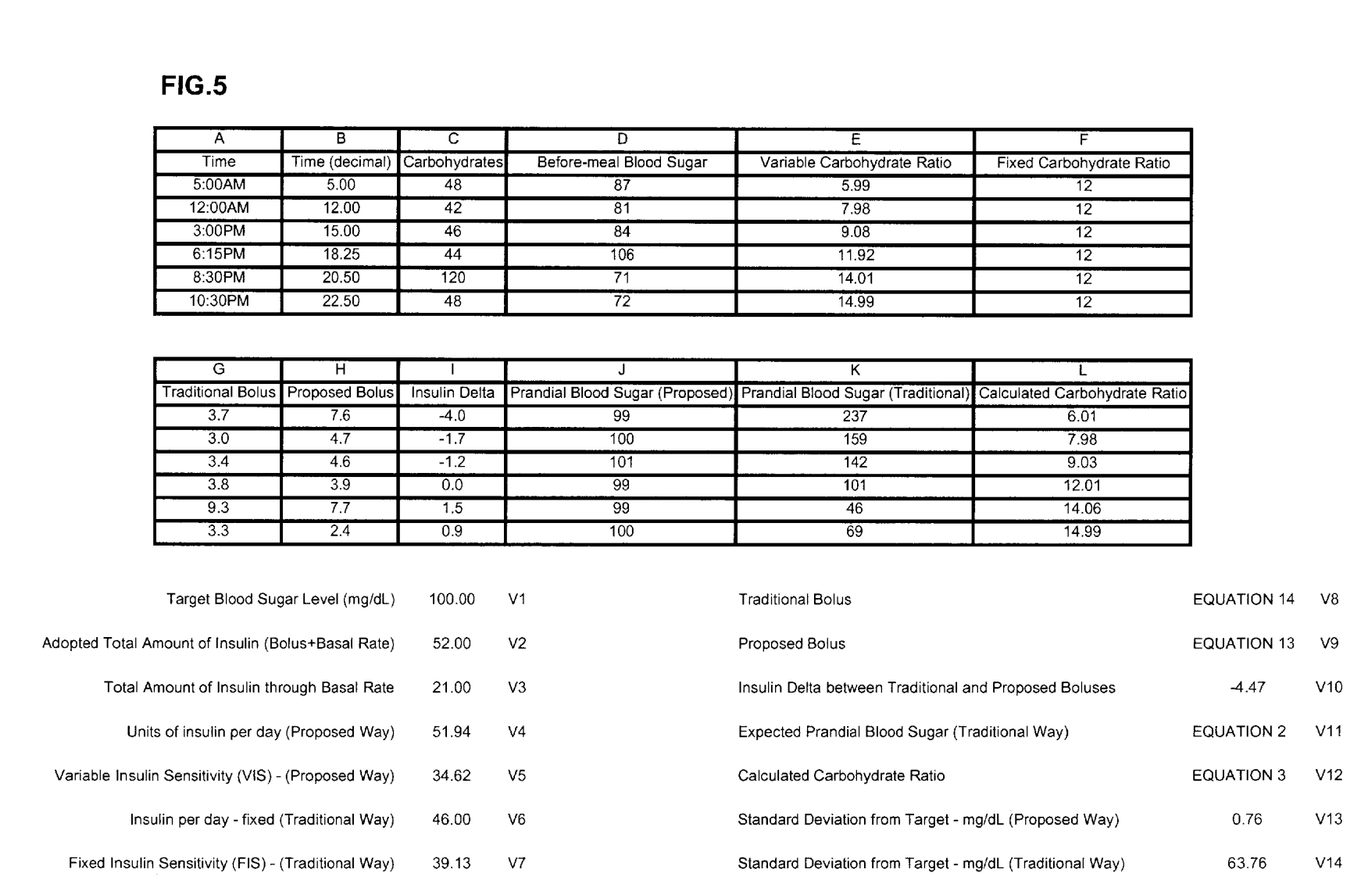
FIG. 5 is a table that facilitates the third interaction of the interactive process that determines the carbohydrate ratio points (item a), whether the user does not have a steady eating habit and he/she needs to go through the 4-day process, in accordance with the invention.
Figure 6:
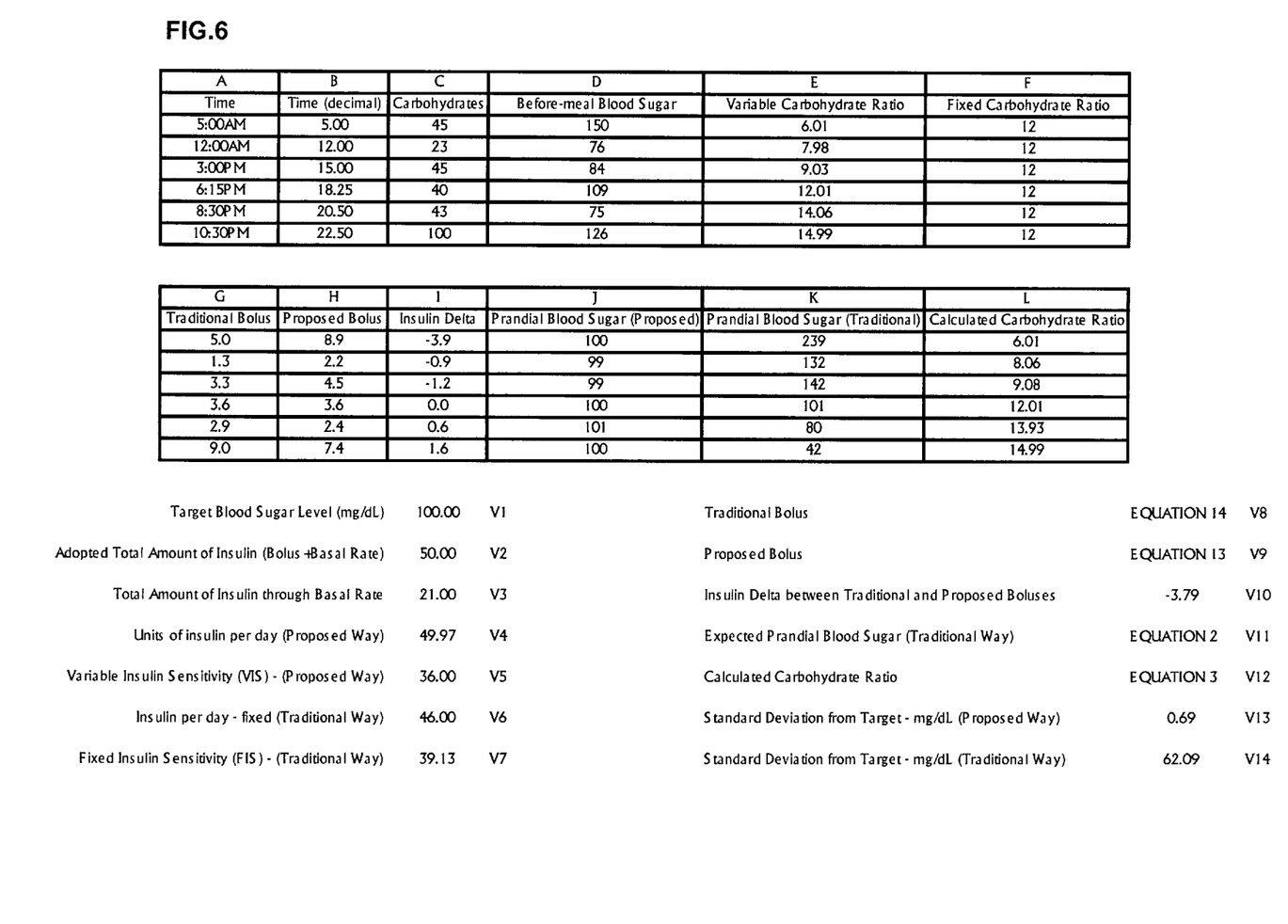
FIG. 6 is a table that facilitates the fourth interaction of the interactive process that determines the carbohydrate ratio points (item a), whether the user does not have a steady eating habit and he/she needs to go through the 4-day process, in accordance with the invention.

The 1-day process (FIG. 2) follows the same description of FIG. 3, as shown through item a, but it does not go through FIG. 6—the process is stopped in the transition to the second table (FIG. 4) and the data of columns B and L are designated the set of points (carbohydrate ratio versus time). A complete illustration of the 4-day process (item a) is seen by FIG. 3 through FIG. 6. The same description is used for the 1-day process, although columns I and K are not used and values of V8 through V12 are not shown, but still calculated (V8 is the mathematical expression of G, as well as V9 is the respective for H, V10 for I, V11 for K, V12 for L), and V13 and V14 are not present in FIG. 2 and in the 1-day process—as shown ahead, V13 and V14 are comparative values, only, as well as V4.

a) Ratio Points: It is a 4-day set with pre-determined and calculated fields. The objective is to calculate a set of points (Carbohydrate Ratio values versus Time) in order to build with them a Carbohydrate Ratio Function (item b). The set of points will be located at column L, either at FIG. 2 or FIG. 6 (dependence of user's option).

In FIG. 1, columns from A through F are populated by user, as well as column J and variables V1, V2, V3, and V6. Columns G, H, I, K, L (and the respective mathematical formulas V8 through V12, as well as V13 and V14)) are calculated as shown below. Columns I and K and variables V13 and V14 are used only for comparison between the prior work and this invention. The right enter-and-calculation sequence is:

1) Enter values for variables V1, V2, V3 and V6.
2) Enter values for columns A, B, C, D, E and F.
3) Calculate V5, V7, G (V8), H (V9), I (V10), V4 and K (V11)—for 1-day method I and K are not used.
4) Enter value for J.
5) Calculate values for L (V12), V13 and V14.—for 1-day method V13 and V14 are not used.
6) If the 1-day method is being used the process ends— otherwise it follows as shown below.

V1—Blood Sugar Reading set by Physician and the user as Target ENTERED BY USER

V2—Adopted Daily Total Amount of Insulin (Personal Forecast for Total Bolus+Total Daily Amount of Insulin through Basal Rate) ENTERED BY USER V3—Total Daily Amount of Insulin through Basal Rate ENTERED BY USER V4—Actual Daily Total Amount of Insulin (Total of H) CALCULATED V5—Variable Insulin Sensitivity=1800/V2 see EQUATION 12 CALCULATED V6—Fixed Daily Total Amount of Insulin ENTERED BY USER V7—Fixed Insulin Sensitivity=1800/V6 see EQUATION 11 CALCULATED V8—Traditional Bolus (G)=((C/F)+(D−V1)/V7) see EQUATION 14 CALCULATED V9—Proposed Bolus (H)=((C/E)+(D−V1)/V5) see EQUATION 13 CALCULATED V10—Total of (I)=(G−H) CALCULATED V11—Expected Prandial Blood Sugar Reading (K)= ((((C/V12)+(D−V1)/V5)−G)*V5)+V1 see EQUATION 2 CALCULATED V12—Calculated Carbohydrate Ratio (L)=C/(((D−V1)/V5)+(D/E)) see EQUATION 3 CALCULATED V13—Standard Deviation comparing V1 and J (this invention) CALCULATED V14—Standard Deviation comparing V1 and K (prior work) CALCULATED Number of rows in all tables (FIG. 3 through FIG. 6) will be either the number of meals that the user normally has throughout the day or a number smaller than the quantity of meals, but at least equals to three. Following is a description of the column headings located in all the tables:

A (TIME) is populated with times that the user eats his/her meals. ENTERED BY USER B (DECIMAL TIME) is populated with the decimal value of the respective time (of A). For example, 5:30 AM is entered as 5.5, as well as 6:15PM is entered as 18.25. ENTERED BY USER C (QUANTITY OF CARBOHYDRATES) is populated with the total quantity of carbohydrates for the respective time (A). ENTERED BY USER D (BLOOD SUGAR READING) is populated with the result of blood sugar test respective to each meal. The blood sugar test will happen after a time pre-set by Physician and the user, considering the action of the insulin (normally two hours). ENTERED BY USER E (VARIABLE CARBOHYDRATE RATIO) is populated, only in FIG. 3, with respective values of column F, FIG. 3—a value pre-set by Physician and the user. In FIG. 4 through FIG. 6, the values for column E come from the column L from the former tables:

Column E, FIG. 3: respective values come from column F, FIG. 3 CARRIED OVER

Column E, FIG. 4: respective values come from column L, FIG. 3 CARRIED OVER

Column E, FIG. 5: respective values come from column L, FIG. 4 CARRIED OVER

Column E, FIG. 6: respective values come from column L, FIG. 5 CARRIED OVER

F (FIXED CARBOHYDRATE RATIO) is populated with a value pre-set by Physician and the user—it follows constant from FIG. 3 through FIG. 6. ENTERED BY USER G (TRADITIONAL BOLUS)—see V8 explanation. CALCULATED H (PROPOSED BOLUS)—see V9 explanation. CALCULATED I (INSULIN DELTA) is populated with respective amounts of difference between G and H (G minus H). V10 is the sum of column, and this column is comparative only. CALCULATED J (PRANDIAL BLOOD SUGAR READING, resulted for use of this invention) is populated with values of blood sugar after a pre-set delay time of respective meals. ENTERED BY USER K (EXPECTED PRANDIAL BLOOD SUGAR READING, resulted for use of the prior work) is populated with expected values for blood sugar that would happen to the user if he/she had followed the prior work, considering the same after-meal, pre-set time by Physician and the user and insulin action. It is shown by EQUATION 2. K is comparative only. CALCULATED $$K=((((C/V12)+(D-V1)/V5)-G)*V5)+V1 \qquad \text{EQUATION 2}$$

L (CALCULATED CARBOHYDRATE RATIO) is the objective of this item b and it is calculated considering that the gap between the blood sugar value and the pre-set target blood sugar can be zeroed adopting the appropriated Carbohydrate Ratio, as shown by EQUATION 3 CALCULATED $$L=C/(((D-V1/V5)+(D/E)) \qquad \text{EQUATION 3}$$

In FIG. 4 the user is required to enter in the values only for C, D, J. Values for A, B, E, F are carried over from FIG. 3. Values for G, H, I, K, L are calculated based on the values for FIG. 4.

In FIG. 5 the user is required to enter in the values only for C, D and J. Values for A, B, E, F are carried over from FIG. 4. Values for G, H, I, K, L are calculated based on the values for FIG. 5.

In FIG. 6 the user is required to enter in the values only for C, D and J. Values for A, B, E, F are carried over from FIG. 5. Values for G, H, I, K, L are calculated based on the values for FIG. 5. After columns B and L in FIG. 6 have been calculated, the respective values of L and B are going to be the base for the next step of this invention, and they will determine a function that will describe how a user's carbohydrate ratio varies throughout the day. V4 is used only to check the accuracy of V2.

b) Ratio Function: The way people absorb carbohydrates can change from time to time. In order to set up a carbohydrate profile this invention proposes to fit under a curve data that are gathered by the user under daily situations. The user is required to input data consistently, following a pre-set time schedule for his/her meals, as described above by explanation related with columns A and B. The previous item a (Ratio Points) calculates the carbohydrate ratio values (column L of FIG. 6) for the itemized times (column B). With this set of points a function can be built in order to predict how user's carbohydrate absorption works throughout the day. The set of points is composed by Calculated Carbohydrate Ratio (column L of FIG. 6) and Time (column B). The function that will be determined will be Calculated Carbohydrate Ratio versus Time, Column L versus Column B, shown by EQUATION 4:

$$L=f(B) \quad \text{EQUATION 4}$$

To calculate a curve such as EQUATION 4, a $4^{th}$-degree polynomial equation is an excellent choice: the adhesion of the calculated curve to the real data is very good and a degree higher than 4 (5, 6 and so on) normally does not allow smooth transition between the points set by column A, but a higher degree can still be used. Having a set of points—(x, y)—we are going to determine a n-degree polynomial equation that will pass through those points, such as shown by EQUATION 5:

$$y=an*(x^n)+a(n-1)*(x^(n-1))+a(n-2)*(x^(n-2))+\ldots +a(1)*(x)+a0 \quad \text{EQUATION 5}$$

For x=xi we have, as shown by EQUATION 6, y=yi:

$$yi=an*(xi^n)+a(n-1)*(xi^(n-1))+a(n-2)*(xi^(n-2))+\ldots +a(1)*(xi)+a0 \quad \text{EQUATION 6}$$

Known and demonstrated least squares method shows that the sum of squared deviation (SD) is such as shown by EQUATION 7:

$$SD=\Sigma[yi-an*(xi^n)+a(n-1)*(xi^(n-1))+a(n-2)*(xi^(n-2))+\ldots +a(1)*(xi)+a0] \quad \text{EQUATION 7}$$

The tabulation of derivations of EQUATION 7 in relation of a1, a2, a3 . . . ap . . . an will result in a system of equations as shown by the following system of equations, equaled to zero:

$$m*a0 + \sum_{i=0}^{n}(xi)*a1 + \ldots + \sum_{i=0}^{n}(xi^n)*an = \sum_{i=0}^{n}yi$$

$$\sum_{i=0}^{n}xi*a0 + \sum_{i=0}^{n}(xi^2)*a1 + \ldots + \sum_{i=0}^{n}xi^(n+1)*an = \sum_{i=0}^{n}(yi)*(xi)$$

$$\sum_{i=0}^{n}(xi^p)*a0 + \sum_{i=0}^{n}(xi^(p+1))*a1 + \ldots + \sum_{i=0}^{n}(xi^(n+p))*an = \sum_{i=0}^{n}(yi)*(xi^p)$$

$$\sum_{i=0}^{n}(xi^n)*a0 + \sum_{i=0}^{n}(xi^(n+1))*a1 + \ldots + \sum_{i=0}^{n}(xi^(2*n))*an = \sum_{i=0}^{n}(yi)*(xi^n)$$

In order to obtain each factor (from a0 to an) the system shown by the system of equations above must be solved, and the solution vector attributed to the mentioned factors (from a0 to an).

To obtain a n-degree polynomial equation a (n+1)-degree system of equations must be solved, and the Gauss Method is the adopted one. A $4^{th}$-degree polynomial equation must be built with the set of points determined in former item (Ratio Points), which means that a $5^{th}$-degree system of equations must be solved, as shown by the following system of equations:

$$\sum_{i=0}^{n}(xi^4)*a4 + \sum_{i=0}^{n}(xi^(3))*a3 +$$

$$\sum_{i=0}^{n}(xi^(2))*a2 + \sum_{i=0}^{n}xi*a1 + \sum_{i=0}^{n}(n)*a0 + \sum_{i=0}^{n}yi$$

$$\sum_{i=0}^{n}(xi^5)*a4 + \sum_{i=0}^{n}(xi^(4))*a3 + \sum_{i=0}^{n}(xi^(3))*a2 +$$

$$\sum_{i=0}^{n}(xi^(2))*a1 + \sum_{i=0}^{n}xi*a0 + \sum_{i=0}^{n}(yi)*(xi)$$

$$\sum_{i=0}^{n}(xi^6)*a4 + \sum_{i=0}^{n}(xi^(5))*a3 + \sum_{i=0}^{n}(xi^(4))*a2 +$$

$$\sum_{i=0}^{n}(xi^(3))*a1 + \sum_{i=0}^{n}(xi^(2))*a0 = \sum_{i=0}^{n}(yi)*(xi^2)$$

$$\sum_{i=0}^{n}(xi^7)*a4 + \sum_{i=0}^{n}(xi^(6))*a3 + \sum_{i=0}^{n}(xi^(5))*a2 +$$

$$\sum_{i=0}^{n}(xi^(4))*a1 + \sum_{i=0}^{n}(xi^(3))*a0 = \sum_{i=0}^{n}(yi)*(xi^3)$$

$$\sum_{i=0}^{n}(xi^8)*a4 + \sum_{i=0}^{n}(xi^(7))*a3 + \sum_{i=0}^{n}(xi^(6))*a2 +$$

$$\sum_{i=0}^{n}(xi^(5))*a1 + \sum_{i=0}^{n}(xi^(4))*a0 = \sum_{i=0}^{n}(yi)*(xi^4)$$

The solution for this system of equations represents the numerical values for a4, a3, a2, a1 and a0—that entered in EQUATION 8 will result in the desired $4^{th}$-degree polynomial equation that will forecast the carbohydrate ratio for a time in the day:

$$y=a4*(x^4)+a3*(x^3)+a2*(xi^2)+a1*x+a0 \quad \text{EQUATION 8}$$

In this invention, the system of equations is fed by the set of points determined in former item (Ratio Points) composed by time and carbohydrate ratio values. The x-axis is related with time and the y-axis is related with carbohydrate ratio values, as shown by EQUATION 9:

$$\text{Carbohydrate Ratio }(t)=a4*(t^4)+a3*(t^3)+a2*(t^2)+a1*t+a0 \quad \text{EQUATION 9}$$

The user determines when his/her carbohydrate ratio profile changed, based on his/her blood sugar readings. When they are not consistent around the target (V1), the user should set up a new profile for his/her carbohydrate ratio, starting over the process with items a) Ratio Points; b) Ratio Function; and c) Bolus. The new carbohydrate ratio function (item b) is determined and turned available to the bolus calculator process (item c). Each factor of the solution of the system of equations is multiplied by the variable t and entered the box 155 of FIG. 9.

c) Bolus: After have entered data related with quantity of carbohydrates and units of insulin forecasted by the user for the current day (box 147 of FIG. 9), the process calculates the insulin ratio (box 149) and transforms the time registered by the computer's clock at the time the software is used in a treatable format to the built-in function (previously determined by item b) and calculates (at box 167) the amount of insulin necessary for the time that the software is being used and the user is eating, combining insulin needed for the carbohydrates (box 163) and blood sugar data (entered at box 165). Box 151 gathers the information about the current time and transforms it in a numeric value—this value is attributed to the variable t and used to make a calculation at line box 155.

The user enters the quantity of insulin that he/she adopts as the total for the current day. When the table is used, the treatable time value is required to be entered, as well as the total daily amount of insulin in order for the Insulin Sensitivity (IS) be calculated by the 1800 Rule, shown by EQUATION 10:

$$IS = 1800/(\text{daily total amount of insulin}) \quad \text{EQUATION 10}$$

Prior to this invention the Insulin Sensitivity was calculated assuming that every day an user would use the same quantity of insulin—a daily and fixed quantity of insulin—shown by EQUATION 11:

$$FIS = 1800/(\text{fixed daily total amount of insulin}) \quad \text{EQUATION 11}$$

FIS: Fixed Insulin Sensitivity

This invention sets the daily quantity of insulin as variable, as shown by EQUATION 12, which sets the Insulin Sensitivity as variable, as well—every time Bolus Calculator is used a new value of insulin quantity is required to be typed in, which allows a more accurate personal forecast to be entered, throughout the day:

$$VIS = 1800/(\text{variable daily total amount of insulin}) \quad \text{EQUATION 12}$$

VIS: Variable Insulin Sensitivity

This process (Bolus, item c) requires the total amount of carbohydrates eaten and the blood sugar reading to determine the amount of insulin needed (bolus) calculated as shown by EQUATION 13:

$$\text{PROPOSED BOLUS} = (BSR - BST)/VIS + (\text{CARBOHYDRATES}/VCR) \quad \text{EQUATION 13}$$

BSR: Blood Sugar Reading BST: Target Blood Sugar
VIS: Variable Insulin Sensitivity
CARBOHYDRATES: Total quantity of carbohydrates eaten in the meal
VCR: Carbohydrate Ratio forecasted for that particular time (as shown either by FIG. 2 or by FIG. 3 through FIG. 6, VCR is set equal to column F only to start the process).

Prior this invention the quantity of insulin (bolus), shown by EQUATION 14, was calculated assuming that the daily quantity of insulin was fixed, as well as the carbohydrate ratio:

$$\text{TRADITIONAL BOLUS} = (BSR - BST)/FIS + (\text{CARBOHYDRATES}/FCR) \quad \text{EQUATION 14}$$

BSR: Blood Sugar Reading BST: Blood Sugar Target
FIS: Fixed Insulin Sensitivity FCR: Fixed Carbohydrate Ratio
CARBOHYDRATES: Total quantity of carbohydrates eaten in the meal The user needs to go through item a (carbohydrate ratio points) prior to item b (carbohydrate ratio function), as well as go through item b prior to item c (bolus).

The user can program and execute item c (Bolus) through a computer system (such as IBM-PC compatible) with an available internal clock, in order to execute the software exactly when he/she is having his/her meal. For example, if the high level language is BASIC, the function TIME$ accesses the current time—box 151—and it transforms this information in a numerical and treatable value to be used by box 155 as variable t.

Prior to executing item c (bolus) the user needs to place at box 155 of FIG. 9, according to his/her personal target, the value for his/her blood sugar. For example, set it as 100 mg/dl—it may change for each user). The numeric value for the carbohydrate ratio, at any given time, is set up by multiplying each component of the carbohydrate ratio vector solution (item b, FIG. 8, box 139)—values of D(1), D(2), D(3), D(4) and D(5)—by the time (variable t, item c, FIG. 9, box 151), this one being graded by the respective exponent (0, 1, 2, 3 or 4), and considering that the grade of the polynomial equation in 4. If another forecasting method is adopted, the same variable (t) should be adopted. The user is required to be aware of his/her total amount of insulin on the day this invention is being used, and put it into the software according to his/her pattern. If the meal which the user is planning to eat differs from his/her pattern as an extra meal, he/she should add a forecasted extra amount of insulin (correspondent to the amount of carbohydrates) in his/her total of the day, and the total amount of insulin units must be changed.

The new total of the day that is entered into the system has its forecast based on the user's self experience: if without this extra meal he/she normally uses an amount of insulin, with this extra meal he/she would use the regular amount of insulin plus the insulin for this extra meal—a simple calculation using EQUATION 13.

The bolus for a meal worthy of 50 g of carbohydrates at breakfast (8 AM) is most likely different than the bolus for the same exact meal—and total amount of carbohydrates—eaten during dinner (8 PM). he absorption will probably be different, as the carbohydrate ratio.

The prior work (traditional way) calculates the bolus using a fixed carbohydrate ratio, during all day. The whole method:

Is not valid for most people,
Is not practical—carrying a calculator and calculating on the spot, and
Is not precise—errors are carried as the calculations evolve.

Bolus (item c) provides an easy way to calculate how many units of short-acting insulin the user needs—either through manual injections or insulin pump, and if embedded in an insulin pump, the user would not even need to carry a handheld—just push the controls on the pump and the bolus would be injected automatically.

This invention allows a much better insulin administration than the traditional way to calculate the bolus, allowing the user to keep track of his/her carbohydrate absorption changes and modify his/her carbohydrate ratio absorption profile throughout the day, while making the calculation practical and automatic.

The process starts (box 1). If any carbohydrate ratio changed or the user does not have a carbohydrate ratio curve (box 3), in either case the user must go through either the 1-day or 4-day process (box 5), and enter the set of data (carbohydrate ratio values versus time) into the function builder (box 7), to determine the carbohydrate function (boxes 63 through 143). Then the user adds it to the bolus calculator part (box 9, and in detail at boxes 145 through 171). Farther this point the whole process is common for both ways—whether the user needs to build a (new) carbohydrate function or not.

So the user enters his/her actual blood sugar value right before the ingestion of the meal, as well as the amount of carbohydrates for that meal and the total quantity of insulin (TQI)—box he/she forecasts for that given day. This forecast is made based on a regular day—if the user is ingesting more carbohydrates than normally he/she does, thus the TQI will be bigger—how big will rely on the user's self experience. The suggested way to deal with this is: if that meal is a regular one, the TQI will be whatever it is for a regular day. If it is a lunch, for example, but the carbohydrate amount is bigger than what the user normally has for a regular day, the user should forecast a higher TQI—he/she can execute the a part of the process (boxes 145 through 163) and have an excellent idea of how bigger this particular bolus would be, and add the difference between a regular meal and this one to TQI. If the meal is an extra snack, the user can also execute part of the process (boxes 145 through 163) and have an excellent idea, now of the extra amount that should be added to TQI.

With the carbohydrate ratio function stored in box 13 (action done at box 9) the process follows through box 17, where the user enters in the meal's carbohydrate quantity, the blood sugar reading and TQI. After that the bolus is calculate (box 15), and displayed (box 19), and the process ends (box 21).

Box 5 is shown in detail by FIG. 2 (1-day option) and FIG. 3 through FIG. 6 (4-day option) and box 5 is explained by item b. Box 5 represents the calculation of the carbohydrate ratio points. Box 7 is shown in detail by FIG. 8 (box 23 through 61, and box 135 through 143) and box 7 is explained by item c.

Box 7 represents the calculation of the carbohydrate ratio function. The user starts this part (box 23) and enters in (box 25) the number of points (it is the number of meals used either by FIG. 2 or FIG. 3 through FIG. 6) through box 35. Box 37 starts the system of equations building process that goes through box 61. Box 63 starts the resolution of the system of equations and it goes through box 133. The solution vector is displayed from box 135 through box 143.

Boxes 15, 17 and 21 are the short form of boxes 145 through 171 (FIG. 9). The final part of the whole process starts (box 145)—the user enters in the total meal's carbohydrate quantity and TQI (box 147). At box 149 the insulin ratio is calculated (EQUATION 12). At box 151 the time is transformed in a numeric and treatable form to be used by box 155, after the user have entered in his/her blood sugar value target at box 153. Box 155 has the carbohydrate ratio function built in, so using information entered through box 151 the carbohydrate ratio value is calculated. The process goes through box 157 for time accuracy check—if the value is negative a message with an advise to check the internal clock is displayed (box 159) and the process is stopped (box 161). Otherwise, if at box 157 the time checking does not point a negative number, the process goes through box 163 (the amount of insulin for the meal's carbohydrate quantity is calculated—the mathematical value is shown by the division after the plus sign, in EQUATION 13). At box 165 the user enters in the actual value of his/her blood sugar reading. At box 167 the adjustment for the box 165 value is done (the division between the equal sign and the plus sign, in EQUATION 13). The value for the bolus is displayed (box 169) and the process ends (box 171).

This value is calculated using the value of time that the user is ready to eat. The user determines how the bolus will be administered, though—whether through an immediate delivery (used for bread, rice, fruits, milk, vegetables, etc), or through a squared bolus, spread for a certain time (for pasta, pizza, fatty, 2-, 3-, 4-hour, high-protein meals), or a combination of both, immediate and squared bolus.

Another factor that should be considered is the time that the bolus will be squared. It also changes time to time, but not in the same pattern and time frame, as the carbohydrate ratio does. The user should be aware to monitor the prandial blood sugar values. If the blood sugar result is after a regular meal and the result is not close to the target (the user decides how close it is acceptable), thus the carbohydrate ratio maybe has changed, and he can go through the 4-day process. If the blood sugar result after a either squared or mixed bolus is not close to the target (the user decides how close it is acceptable), thus the way it is administered must be changed—for example, if the bolus was a pure squared one, for 2 hours, the user needs either change the time it was squared (from 2 hours to 1.5 hour or 2.5 hours) or go to a mixed bolus, such as ⅓ through immediate delivery and ⅔ squared. As the time passes by and changes occur, the proportion can be changed (⅔ and ⅓, or ½ and ½ . . . ), even becoming pure immediate delivery or pure squared.

Bolus (item c) provides an easy way to calculate how many units of short-acting insulin he/she needs—either through manual injections or insulin pumps, and if embedded in an insulin pump, the user would not even need to carry a handheld—just push the controls on the pump and the bolus would be injected automatically. This invention allows a much better insulin administration than the traditional way to calculate the bolus, allowing the user to keep track of his/her carbohydrate absorption changes and modify his/her carbohydrate ratio absorption profile throughout the day, while making the calculation practical and automatic. The process starts (box 1). If any carbohydrate ratio changed or the user does not have a carbohydrate ratio curve (box 3), in either case the user must go through either the 1-day or 4-tab process (box 5), and enter them into the function builder (box 7), to determine the carbohydrate function (box 7, shown in details by boxes 63 through 143). Then the user adds it to the bolus calculator part (box 9, shown in detail by boxes 145 through 171). Farther this point the whole process is common for both ways—whether the user needs to build a (new) carbohydrate function or not. So the user enter (box 17) his/her actual blood sugar value right before the ingestion of the meal, as well as the amount of carbohydrates for that meal and the total quantity of insulin (TQI) that he/she forecasts for that given day. This forecast is made based on a regular day—if the user is ingesting more carbohydrates than normally he/she does, thus the TQI will be bigger—how big will rely on the user's self experience.

The suggested way to deal with this is: if that meal is a regular one (as breakfast, lunch, dinner or normally taken snack), the TQI will be whatever it is for a regular day. But if the meal is a lunch, for example, but the carbohydrate amount is bigger than what the user normally ingests for a regular day, the user should forecast a higher TQI—he/she can execute a part of the process (boxes 145 through 163) and have an excellent idea of how bigger this particular bolus would be, and add the difference between a regular meal and this one to TQI. If the meal is an extra snack, the user can also execute part of the process (boxes 145 through 163) and have an excellent idea, now of the total extra amount that should be added to TQI, hence it is an extra snack. With the carbohydrate ratio function stored in box 13 (action done at box 9) the process follows through box 17, where the user enters in the meal's carbohydrate quantity, the blood sugar reading and TQI. After that the bolus is calculate (box 15), and displayed (box 19), and the process ends (box 21). Box 5 is shown in detail by FIG. 2 (1-day option) and FIG. 3 through FIG. 6 (4-day option) and box 5 is explained by item b. Box 5 represents the way of calculation of the carbohydrate ratio points.

Box 7 is shown in detail by FIG. 8 (box 23 through 61, and box 135 through 143) and box 7 is explained by item c. Box 7 represents the calculation of the carbohydrate ratio function. The user starts this part (box 23) and enters in (box 25) the number of points (it is the number of meals used either by FIG. 2 or FIG. 3 through FIG. 6) through box 35. Box 37 starts the system of equations building process that goes through box 61. Box 63 starts the resolution of the system of equations and it goes through box 133. The solution vector is displayed from box 135 through box 143. Boxes 15, 17 and 21 are the short form of boxes 145 through 171 (FIG. 9). The final part of the whole process starts (box 145)—the user enters in the total meal's carbohydrate quantity and TQI (box 147). Through box 149 the insulin ratio is calculated (EQUATION 12). Through box 151 the time is transformed in a numeric and treatable form to be used by box 155, after the user have entered in his/her blood sugar value target at box 153. Box 155 has the carbohydrate ratio function built in, so using information entered through box 151 the carbohydrate ratio value is calculated. The process goes through box 157 for time accuracy check—if the value is negative a message with an advise to check the internal clock is displayed (box 159) and the process is stopped (box 161). Otherwise, if through box 157 the time checking does not point a negative number, the process goes through box 163—the amount of insulin for the meal's carbohydrate quantity is calculated—the mathematical value is shown by the division after the plus sign, in EQUATION 13. Through box 165 the user enters in the actual value of his/her blood sugar reading. Through box 167 the adjustment for the box 165 value is done (the division between the equal sign and the plus sign, in EQUATION 13). The value for the bolus is displayed (BOX 169) and the process ends (box 171).

What is claimed is:

1. A method of determining a diabetic person's required amount of insulin (Bolus) to be injected into person in order to maintain proper blood sugar levels, comprising the steps of:

determining the person's blood sugar level;

determining the amount of carbohydrates and sugar ingested by the person;

determining the variable daily total amount of insulin the person forecasts for a single day; and calculating the appropriate amount of insulin, based upon the measured blood sugar level, the amount of carbohydrates and sugar ingested by the person and the carbohydrate ratio, being the relation between carbohydrates intake and insulin needed to digest those carbohydrates, and an amount of insulin the person forecasts for a single day, a variable daily total amount of insulin forecasted by the person, by utilizing the following formula:

$$Bolus=(C/L)+(BSR-BST)/VIS$$

wherein C=total amount of carbohydrates, L=corrected carbohydrate ratio, BST=target blood sugar, BSR= blood sugar reading, and VIS=Insulin sensitivity calculated by diving 1800 by a variable daily total amount of insulin forecasted by the person.

2. The method as claimed in claim 1 wherein the step of determining the person's bold sugar level comprises determining the prandial blood sugar level using a glucose concentration measuring system.

3. An apparatus for determining a diabetic person required amount of insulin to be injected into the person in order to maintain proper blood sugar levels, comprising:

a measuring means for determining the person's blood sugar level;

a calculating means for determining the appropriate amount of insulin, based upon a) the measured blood sugar level, b) an amount of carbohydrates and sugar ingested by the person and c) a corrected carbohydrate ratio, being the relation between carbohydrates intake and insulin needed to digest those carbohydrates, and an amount of insulin the person forecasts for a single day, a variable daily total amount of insulin forecasted by the person, by utilizing the following formula:

$$BOLUS=(C/L)+(BSR-BST)/VIS$$

wherein C=total amount of carbohydrates, L=corrected carbohydrate ratio, BST=target blood sugar, BSR= blood sugar reading, and VIS=Insulin sensitivity calculated by diving 1800 by the variable daily total amount of insulin forecasted by the person.

4. The apparatus as claimed in claim 3 wherein the measuring means for determining the person's bold sugar level is a glucose concentration measuring system.

5. A method of determining a person's carbohydrate ratio, being the relation between carbohydrates intake and insulin needed to digest those carbohydrates, for any given time comprising the steps of;

determining the person's blood sugar level immediately before a meal;

determining the amount of carbohydrates and sugar ingested by the person during the meal;

determining an initial amount of insulin (G) to be injected immediately before the meal calculated by the following formula:

$$G=(C/CR)+(BSR-BST)/FIS$$

wherein C=total amount of carbohydrates in the meal, CR=initial carbohydrate ratio assigned to the person, BSR=the person's blood sugar determining the person's blood sugar level (J) after ingested meal's digestion has been completed;

determining a corrected carbohydrate ratio (L) for the time the meal was ingested, calculated by the following formula:

$$L=C/(((J-BST)/ViS)+(C/E))$$

wherein L=Corrected Carbohydrate Ratio, C=total amount of carbohydrates in the meal, J=Blood Sugar Reading after digestion, BST=target blood sugar assigned to the person, VIS=Forecasted Insulin Sensitivity calculated by diving 1800 by the variable daily total amount of insulin forecasted by the person, E=initial person's carbohydrate ratio.

6. A method in accordance with claim 5 for determining a person's variable insulin sensitivity, further comprising the steps of:

determining the variable daily total amount of insulin the person forecasts for the day for the meals to be eaten (VIS); and determining person's variable insulin sensitivity calculated by the following formula:

$$ViS = 1800/\text{variable daily total amount of insulin forecasted by the person.}$$

7. A method in accordance with claim 5 for determining a person's carbohydrate ratio, further comprising the steps of:
- determining at least three (3) Corrected Carbohydrate Ratios (L) for different times, covering the period of time person is used to ingest food; and
- determining a curve that represents persons carbohydrate ratio as function of time.

8. A method of determining a person's required amount of insulin (Bolus) to be injected into person in order to achieve person's blood sugar level target after ingested food has been digested (or after a chosen period of time) comprising the steps of:
- determining the person's blood sugar level before a meal (BSR);
- determining the amount of carbohydrates and sugar ingested by the person during that meal (C);
- determining the variable insulin sensitivity (VIS) being calculated by diving 1800 by the variable daily total amount of insulin forecasted by the person;
- determining the Corrected Carbohydrate Ratio (L) for the time of the day the meal is being eaten, calculated by the following formula:

$$L = C/(((BSR-BST)/VIS)-(C/E))$$

determining the amount of insulin (Bolus) by the following formula:

$$Bolus = (C/L) + (J-BST)/VIS$$

wherein C=total amount of carbohydrates for the meal, L=Corrected Carbohydrate Ratio for the time the meal is being eaten, J=person's blood sugar reading immediately before the meal, BST=target blood sugar, VIS=Forecasted Insulin Sensitivity calculated by diving 1800 by the variable daily total amount of insulin forecasted by the person, E=initial person's carbohydrate ratio.

\* \* \* \* \*